United States Patent
Siddanahalli Ninge Gowda et al.

(10) Patent No.: US 12,070,357 B2
(45) Date of Patent: Aug. 27, 2024

(54) SYSTEM AND METHOD FOR AUTOMATIC ASSOCIATION AND DISPLAY OF VIDEO LOOP SUBJECT MATTER FOR ENHANCED IDENTIFICATION

(71) Applicant: GE Precision Healthcare LLC, Wauwatosa, WI (US)

(72) Inventors: Arun Kumar Siddanahalli Ninge Gowda, Bangalore (IN); Srinivas Koteshwar Varna, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 264 days.

(21) Appl. No.: 17/546,245

(22) Filed: Dec. 9, 2021

(65) Prior Publication Data

US 2023/0181163 A1   Jun. 15, 2023

(51) Int. Cl.
*A61B 8/08* (2006.01)
*A61B 8/00* (2006.01)
*G06N 20/00* (2019.01)

(52) U.S. Cl.
CPC ............ *A61B 8/5207* (2013.01); *A61B 8/465* (2013.01); *A61B 8/5215* (2013.01); *G06N 20/00* (2019.01)

(58) Field of Classification Search
CPC .............................. A61B 8/461; A61B 8/5223
See application file for complete search history.

(56) References Cited

U.S. PATENT DOCUMENTS

| 10,405,832 B2 | 9/2019 | Kim et al. |
| 2004/0019276 A1 | 1/2004 | Kim et al. |
| 2007/0106146 A1 * | 5/2007 | Altmann ............. A61B 8/12 600/407 |
| 2012/0108960 A1 | 5/2012 | Halmann et al. |
| 2013/0332868 A1 * | 12/2013 | Kaftan ............. G06T 19/00 715/764 |
| 2017/0235903 A1 * | 8/2017 | McLaughlin ....... G01S 7/52084 715/708 |

(Continued)

FOREIGN PATENT DOCUMENTS

WO   WO-2018195946 A1 *  11/2018  ............. A61B 8/00

OTHER PUBLICATIONS

WO-2018195946-A1 (Year: 2018).*

*Primary Examiner* — Joel Lamprecht
*Assistant Examiner* — Nyrobi Celestine
(74) *Attorney, Agent, or Firm* — Boyle Fredrickson S.C.

(57) ABSTRACT

An imaging system and a method for displaying information regarding the subject matter of an ultrasound image or ultrasound video loop on a display includes the steps of detecting one or more organs in the ultrasound image or ultrasound video loop, creating a representative thumbnail image utilizing the ultrasound image or a frame of the ultrasound video loop, selecting an organ icon representing the one or more organs detected in the ultrasound image or ultrasound video loop, and presenting the organ icon in association with the thumbnail image on the display. The system and method can also create search-identifiable information relating to the one or more organs detected in the ultrasound image or ultrasound video loop, and store the search-identifiable information in the electronic memory in association with the image or the image video loop and the thumbnail image with the organ icon.

19 Claims, 7 Drawing Sheets

(56) References Cited

U.S. PATENT DOCUMENTS

| | | |
|---|---|---|
| 2019/0012432 A1 | 1/2019 | Sokulin et al. |
| 2019/0125301 A1* | 5/2019 | Jago ........................ A61B 8/463 |
| 2019/0183451 A1* | 6/2019 | Yu ........................... G06F 16/50 |
| 2020/0205783 A1* | 7/2020 | Shiran .................... A61B 8/468 |
| 2021/0128116 A1* | 5/2021 | Xu ........................ G06T 7/0016 |
| 2021/0177373 A1* | 6/2021 | Xie .......................... G06N 3/04 |
| 2022/0061812 A1* | 3/2022 | Morrise ............... A61B 8/5223 |

* cited by examiner

SYSTEM AND METHOD FOR AUTOMATIC ASSOCIATION AND DISPLAY OF VIDEO LOOP SUBJECT MATTER FOR ENHANCED IDENTIFICATION

BACKGROUND OF THE INVENTION

The invention relates generally to imaging systems, and more particularly to structures and methods of displaying images generated by the imaging systems.

An ultrasound imaging system typically includes an ultrasound probe that is applied to a patient's body and a workstation or device that is operably coupled to the probe. The probe may be controlled by an operator of the system and is configured to transmit and receive ultrasound signals that are processed into an ultrasound image by the workstation or device. The workstation or device may show the ultrasound images through a display device operably connected to the workstation or device.

After creation by the ultrasound imaging system, the images can be stored in any suitable electronic storage format and/or electronic storage device operably connected to the ultrasound imaging system. Upon accessing the stored images, the images can be presented on the display device in a reduced size format in order to enable multiple stored images to be presented on the display device at the same time, such that the operator/user can navigate through them to select and review specific images of interest.

In the case of video loops obtained and/or created by the ultrasound imaging device, these loops are stored in the electronic storage device in association with a representative image selected from the video loop that is utilized to identify the loop. Upon accessing the electronic storage device to locate the stored video loop, the representative image is presented on the display using the representative image with a playback icon disposed over the representative image to identify the image as indicating a video loop.

With this identification system, when the user of an ultrasound imaging system wants to search through the stored video loops to locate one or more video loops associated with a particular organ/anatomical structure, the user must review the available stored loops based on the representative image or thumbnail image associated with each of the loops. However, often the thumbnail image associated with the stored video loop might not be an ultrasound image or frame in the video loop that corresponds to the organ captured within that video loop. For example, on most occasions the first frame or the last frame of the stored ultrasound video loop will often be chosen as the representative thumbnail image for the stored video loop. However, these frames often do no show the organ that is the main focus of the video loop for a variety of reasons, e.g., the video loop begins at a time prior to the placement of the ultrasound probe over the organ to be imaged.

Also, in the presentation of the stored video loops, the playback icon is centered on the thumbnail image so that user can readily identify that the associated file is a video loop and can easily select or click directly on the playback icon to start playing the stored video loop. The playback icon is disposed in the center of the thumbnail image rather than at one of the corners as clicking on an icon placed on a corner of a thumbnail image is extremely hard and error prone, particularly on touchscreen-based display devices including those with limited screen sizes, including smartphones and tablet devices.

Further, regardless of whether the representative thumbnail image associated with the stored video loop corresponds to the frame in the stored video loop where the organ or anatomical structures that are the subject of the video loop are present, the details of organs and/or anatomical structures present within that representative thumbnail image are overlapped by the playback icon. Because the thumbnail images are relatively very small in comparison with the image size for the images forming the stored video loop, the presence of the play button on the small thumbnail images increases the difficulty of identifying the details of the type of organ/structure illustrated within the thumbnail image. This problem is even more significant when the display device associated with the ultrasound imaging system on which the thumbnail images are presented has a very small display area, e.g., mobile devices like smartphones and tablet devices, or even with larger displays when there are large number of thumbnail images identifying stored video loops that need to be displayed for the user to navigate and choose a particular loop.

As a result of these limitations concerning the selection and presentation of the representative thumbnail images for a stored video loop, it is often very difficult to easily identify the organs/anatomical structures associated with the stored video loops through the thumbnail images without having to manually review or playback each stored video loop when searching for a stored video loop associated with the desired organs/anatomical structures, making the searching process very time consuming.

Therefore, it is desirable to develop a system and method for the presentation of thumbnail images identifying stored video loops on a screen of a display device that notifies the user of the organs or other relevant anatomical structures within the ultrasound video loop which may not be readily apparent from the thumbnail image.

BRIEF DESCRIPTION OF THE DISCLOSURE

According to one exemplary aspect of the disclosure, a method for displaying information regarding the subject matter of an ultrasound image or ultrasound video loop on a display includes the steps of detecting one or more organs in the ultrasound image or ultrasound video loop, creating a representative thumbnail image utilizing the ultrasound image or a frame of the ultrasound video loop, selecting an organ icon representing the one or more organs detected in the ultrasound image or ultrasound video loop, and presenting the organ icon in association with the thumbnail image on the display.

According to another exemplary aspect of the disclosure, an imaging system for displaying images obtained by the imaging system on a display including an imaging probe adapted to obtain image data on an object to be imaged, a processor operably connected to the probe to form one of an image or an image video loop from the image data and to form a thumbnail image representative of the image or image video loop; and a display operably connected to the processor for presenting the image or the image video loop on the display, wherein the processor is configured to implement at least one of an algorithm, an artificial intelligence or a machine learning method to detect one or more organs in the image or the image video loop, to select an organ icon representing the one or more organs detected in the ultrasound image or ultrasound video loop, and to present the organ icon in association with the thumbnail image of the image or image video loop on the display.

According to still another exemplary aspect of the disclosure, an imaging system for displaying images obtained by the imaging system on a display including an imaging probe adapted to obtain image data on an object to be imaged, a processor operably connected to the probe to form one of an image or an image video loop from the image data and to form a thumbnail image representative of the image or image video loop, an electronic memory operably connected to the processor, and a display operably connected to the processor for presenting the image or the image video loop on the display, wherein the processor is configured to implement at least one of an algorithm, an artificial intelligence or a machine learning method to detect one or more organs in the image or the image video loop, to select an organ icon representing the one or more organs detected in the ultrasound image or ultrasound video loop, to store the thumbnail and organ icon in association with the image or image video loop in the electronic memory, and to present the organ icon in association with the thumbnail image of the image or image video loop on the display.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. One or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Although the various embodiments are described with respect to an ultrasound imaging system, the various embodiments may be utilized with any suitable imaging system, for example, X-ray, computed tomography, single photon emission computed tomography, magnetic resonance imaging, or similar imaging systems.

Figure 1:
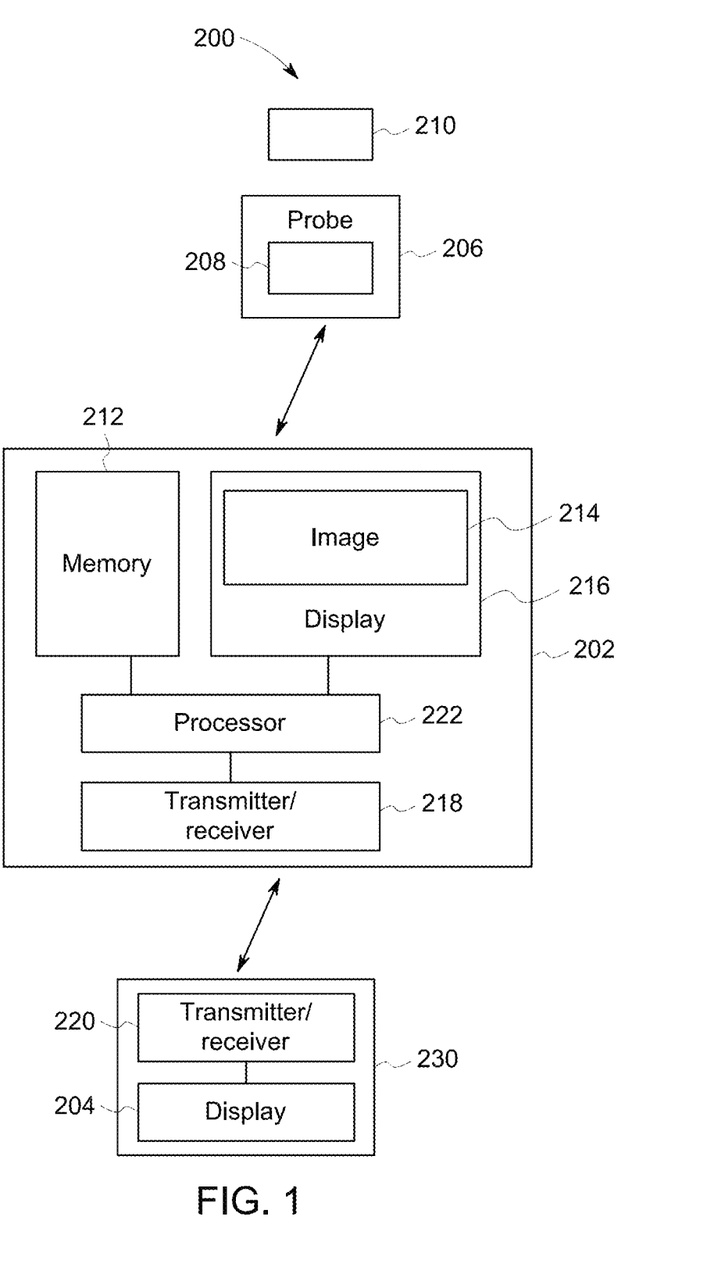
FIG. 1 is a schematic block diagram of an imaging system formed in accordance with an embodiment.

FIG. 1 is a schematic view of an imaging system 200 including an ultrasound imaging system 202 and a remote device 230. The remote device 230 may be a computer, tablet-type device, smartphone or the like that can be an off-the-shelf device, or a device dedicated for use as the remote device 230 in conjunction with the imaging system 202. The term "smart phone" as used herein, refers to a portable device that is operable as a mobile phone and includes a computing platform that is configured to support the operation of the mobile phone, a personal digital assistant (PDA), and various other applications. Such other applications may include, for example, a media player, a camera, a global positioning system (GPS), a touchscreen, an internet browser, Wi-Fi, etc. The computing platform or operating system may be, for example, Google Android™, Apple iOS™, Microsoft Windows™, Blackberry™, Linux™, etc. Moreover, the term "tablet-type device" refers to a portable device, such as for example, a Kindle™ or iPad™. The remote device 230 may include a touchscreen display 204 that functions as a user input device and a display. The remote device 230 communicates with the ultrasound imaging system 202 to display an image 214 based on image data acquired by the ultrasound imaging system 202 on the display 204. The remote device 230 also includes any suitable components for image viewing, manipulation, etc., as well as storage of information relating to the image 214.

A probe 206 is in communication with the ultrasound imaging system 202. The probe 206 may be mechanically coupled to the ultrasound imaging system 202. Alternatively, the probe 206 may wirelessly communicate with the imaging system 202. The probe 206 includes transducer elements/an array of transducer elements 208 that emit ultrasound pulses to an object 210 to be scanned, for example an organ of a patient. The ultrasound pulses may be backscattered from structures within the object 210, such as blood cells or muscular tissue, to produce echoes that return to the transducer elements 208. The transducer elements 208 generate ultrasound image data based on the received echoes. The probe 206 transmits the ultrasound image data to the ultrasound imaging system 202 operating the imaging system 200. The image data of the object 210 acquired using the ultrasound imaging system 202 used to form the image 214 may be two-dimensional or three-dimensional image data, such that the image 214 can be an ultrasound image and/or video loop 214. In another alternative embodiment, the ultrasound imaging system 202 may acquire four-dimensional image data of the object 210. In generating the image/video loop 214, the processor 222 is also configured to automatically identify organs and/or other anatomical structures 224 within image/video loop 214, and to provide identifications of those organs and/or other anatomical structures 224 within the image/video loop 214.

The ultrasound imaging system 202 includes a memory 212 that stores the ultrasound image data. The memory 212 may be a database, random access memory, or the like. A processor 222 accesses the ultrasound image data from the memory 212. The processor 222 may be a logic based device, such as one or more computer processors or microprocessors. The processor 222 generates an image based on the ultrasound image data. After formation by the processor 222, the image/video loop 214 is presented on a display 216 for review, such as on display screen of a cart-based ultrasound imaging system 202 having an integrated display/monitor 216, or an integrated display/screen 216 of a laptop-based ultrasound imaging system 200, optionally in real time during the procedure or when accessed after completion of the procedure.

In one exemplary embodiment, the ultrasound imaging system 202 can present the image/video loop 214 on the associated display/monitor/screen 216 along with a graphical user interface (GUI) or other displayed user interface. The image/video loop 214 may be a software based display that is accessible from multiple locations, such as through a web-based browser, local area network, or the like. In such an embodiment, the image/video loop 214 may be accessible remotely to be displayed on a remote device 230 in the same manner as the image/video loop 214 is presented on the display/monitor/screen 216.

The ultrasound imaging system 202 also includes a transmitter/receiver 218 that communicates with a transmitter/receiver 220 of the remote device 230. The ultrasound imaging system 202 and the remote device 230 may communicate over a direct peer to peer wired/wireless connection or a local area network or over an internet connection, such as through a web-based browser.

An operator may remotely access imaging data stored on the ultrasound imaging system 202 from the remote device 230. For example, the operator may log onto a virtual desktop or the like provided on the display 204 of the remote device 230. The virtual desktop remotely links to the ultrasound imaging system 202 to access the memory 212 of the ultrasound imaging system 202. Once access to the memory 212 is obtained, the operator may select image data to view. The image data is processed by the processor 222 to generate an image/video loop 214. For example, the processor 222 may generate a DICOM image/video loop 214. The ultrasound imaging system 202 transmits the image/loop 214 to the display 204 of the remote device 230 so that the image/video loop 214 is viewable on the display 204.

Figure 2:
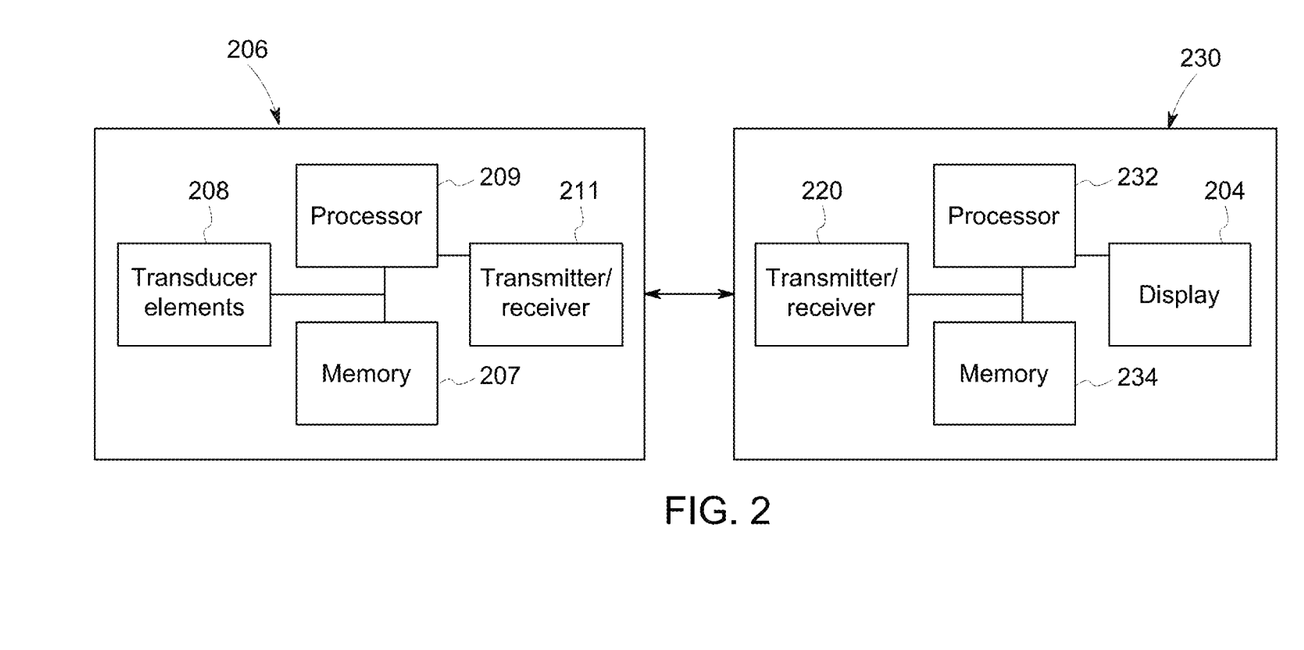
FIG. 2 is a schematic block diagram of an imaging system formed in accordance with another embodiment.

Looking now at FIG. 2, in an alternative embodiment, the imaging system 202 is omitted entirely, with the probe 206 constructed to include memory 207, a processor 209 and transceiver 211 in order to process and send the ultrasound image data directly to the remote device 230 via a wired or wireless connection. The ultrasound image data is stored within memory 234 in the remote device 230 and processed in a suitable manner by a processor 232 operably connected to the memory 234 to create and present the image/video loop 214 on the remote display 204.

Figure 3:
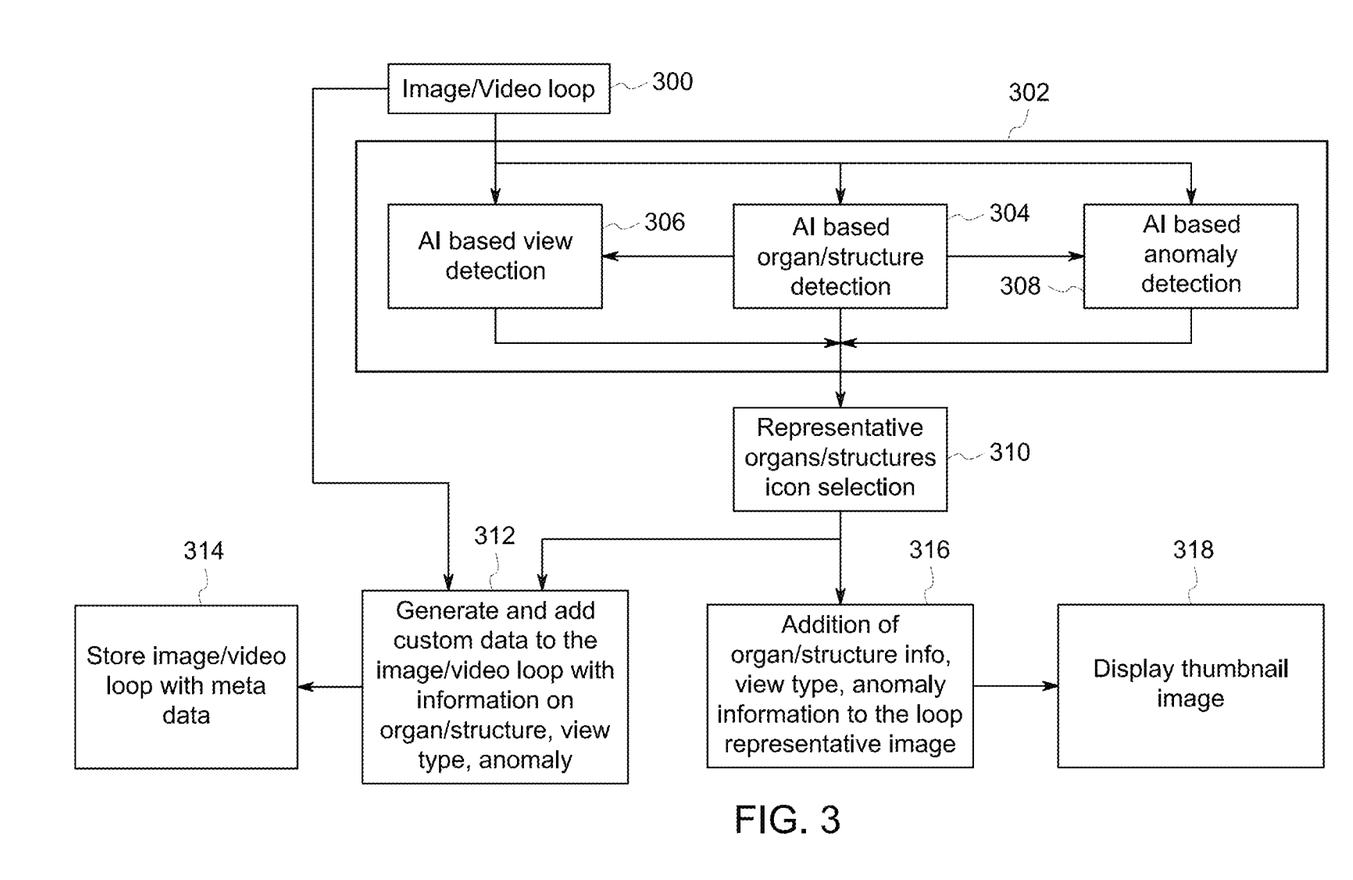
FIG. 3 is a flowchart of a method for operating the imaging system shown in FIG. 1 or FIG. 2 in accordance with an embodiment.

In either embodiment, referring now to FIG. 3, after the creation of the image/video loop 214 by the processor 222,232 in block 300, in block 302 the processor 222,232 also performs one or more detection analyses on the image/individual frames of the video loop 214. In the illustrated exemplary embodiment, the analysis performed in block 302 can include one or more of the detection of: 1.) the organ(s)/anatomical structure(s) present within the image/video loop frame(s) 214 in block 304; 2.) the detection of the view direction or angle associated with the organ(s)/anatomical structure(s) represented within the image/video loop frame(s) 214 in block 306, and/or 3.) the detection of any anomalies in the organ(s)/anatomical structure(s) illustrated within the image/video loop frame(s) 214 in block 308. For a video loop 214, the processor 222,232 will perform the selected analyses on each individual image, and/or frames of the video loop 214. The detection of the organ(s)/anatomical structure(s) within the image/video loop frame(s) 214 in block 304, the view of the organ(s)/anatomical structure(s) within image/video loop frame(s) 214 in block 306 and/or any anomalies in the organ(s)/anatomical structure(s) within the image/video loop frame(s) 214 in block 308 are performed by the processor 222,232 using known identification processes and/or algorithms for ultrasound or other imaging system image generation. For example, traditional image processing techniques, or Artificial Intelligence (AI) based-approaches including machine learning (ML) and deep learning (DL), among others, or a combination of both can be used to identify organ(s)/anatomical structure(s), views and anomalies present within the image/video loop frame(s) 214. For AI based identification approaches the end goal of identifying organ(s)/anatomical structure(s), and anomalies present within the image/video loop frame(s) 214 could be formulated as either image segmentation, image classification or object localization problem. Likewise, the goal of view detection of organ/anatomical structures within the image/video loop frame(s) 214 could be formulated as a classification problem. Though traditional ML based approaches like support vector machines (SVM), random forest (RF), etc., can be used to solve these problems, convolutional neural networks (CNN), a class of deep learning (DL) based models, are best suited for such tasks yielding much better accuracy and adaptability across various imaging conditions. The information about the detected organ/anatomical structure within an image/video loop frame(s) from step 304 can also be used as an additional input along with the input image/video loop frame(s) by the view detection 306 and anomaly detection 308 models to improve the accuracy of their respective tasks. Though in the exemplary embodiment for the organ/structure detection, view detection and anomaly detection functionalities are shown to be implemented by separate AI based models in blocks 304, 306 and 308, they could as well be combined and realized within a single multi-headed DL based model where each of the individual heads implements a separate functionality namely organ/anatomical structure detection, view detection or anomaly detection. Based on multi-task learning such multi-headed DL models share common backend layers relevant for all functionalities/tasks followed by task specific/functionality specific layers that are trained/tuned to perform well on their respective tasks/functionalities.

With regard to the process performed in block 304 by the processor 222,232 to determine the presence of one or more organs within the image/video loop 214, during the analysis of the image/video loop 214, the processor 222,232 can utilize threshold values stored in memory 212,234. These threshold values, which can be preset and/or modified by the user as desired, are utilized by the processor 222,232 to determine if the image/video loop 214 contains enough of a representation of the organ(s)/anatomical structure(s) within the image/video loop 214 for an organ icon 256 to be included with the thumbnail image 250 of the image/video loop 214. While the threshold value can be set as desired in any suitable format, in an exemplary embodiment the threshold value can be based off of a percentage of the total area of a single image 214 for an ultrasound image 214, and/or the total number, or percentage of individual frames forming the video loop 214 that contain at least a portion of the selected organ therein. For example, if an analysis of an image 214 shows an organ present in at least 25% of the total area of the image 214, or if analysis of a video loop 214 shows an organ present in at least 15% of the individual frames of the video loop 214, the organ has exceeded the threshold value for the image/video loop 214, and the processor 222,232 determines that a representative indicator 240 identifying that organ/anatomical structures should be included with the thumbnail image 250 for the image/video loop 214.

From block 304, when the processor 222,232 has detected a particular organ/anatomical structure within the image/video loop frame 214, the processor 222,232 continues to block 310 where the processor 222,232 selects the representative identifier(s) 240 for use in association with the image/video loop 214. The identifier 240 corresponds to the organ/anatomical structure detected in the image/video loop 214 to provide an indication of the subject matter present in the image/video loop 214.

Once the representative identifier 240 has been selected, in block 312 the processor 222,232 proceeds to generate custom data/search-identifiable information for the video loop 214 based off of the representative identifier 240. In an exemplary embodiment, this process involves the processor 222,232 creating the classification or search-identifiable information regarding the detected organ/anatomical structure to the electronic storage location or file in memory 212, 234 where the stored image/video loop 214 is located. This information can be added to the stored image/video loop 214 in any suitable manner in block 314, such as by adding the information in the form of custom meta-data or custom tags to the electronic file or electronic storage location containing the stored image/video loop 214 in memory 212,234. In this manner, the stored image/video loop 214 can be more readily located and accessed in a search for images/video loops 214 relating to the organ/anatomical structure detected by the processor 222,232, such as in a keyword search including terms contained within the meta-data or tags added to the stored image/video loop 214 by the processor 222,232.

In addition to the information added to the stored image/video loop 214, in block 316 the processor 222,232 can use the representative identifier 240 to generate information to be added directly to a thumbnail image 250 used as a visual representation of the stored image/video loop 214. The thumbnail image 250 is selected from one of the frames forming the video loop 214 and is utilized as a visual identifier for the stored video loop 214 when presented on a display 216, 204. The thumbnail image 250 includes the selected frame from the video loop 214 as well as a playback icon 252 overlaid onto the center of the thumbnail image 250. The playback icon 252 serves as a direct link to the stored video loop 214 in the memory 212,234 and can be selected by the user in any known manner to initiate the playback of the video loop 214, either within the frame 254 of the thumbnail image 250, or in a separate frame or window (not shown) on the display 216,204 that opens after selection of the playback icon 252.

Within the thumbnail image 250, the representative identifier 240 in one exemplary embodiment illustrated in FIGS. 6A-6E can take the form an organ icon 256 positioned on the thumbnail image 250. The organ icon 256 is positioned in a location within the thumbnail image 250 that does not interfere with the playback icon 252 and provides a clear and readily viewable indication of the organ/anatomical structure that is the subject of the video loop 214. The organ icon 256 can be presented in any suitable color in order to delineate the organ icon 256 from the remainder of the thumbnail image 250. In the illustrated exemplary embodiments of FIGS. 6A-6E, the organ icon 256 can take the form of a kidney (FIG. 6A), a bladder (FIG. 6B), a liver (FIG. 6C), a heart (FIG. 6D), or a pair of lungs (FIG. 6E), though other shapes and colors for the organ icon 256 are also contemplated as being within the scope of the present disclosure.

After addition of the organ icon 256 to the thumbnail image 250, the revised thumbnail image 250 is stored in block 318 such that the modified thumbnail image 250 including the organ icon 256 can be displayed when the image/video loop 214 associated with the modified thumbnail image 250 is presented on a display 216,204.

Figure 6A:
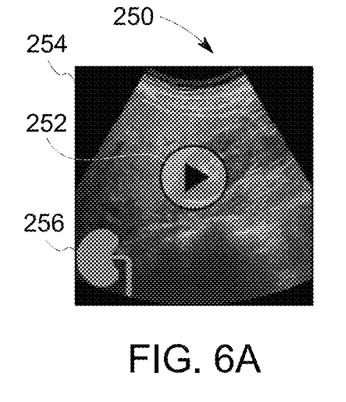
FIGS. 6A-6H are schematic views of individual thumbnail images representing stored video loops in accordance with different embodiments.
Figures 6B, 6C:
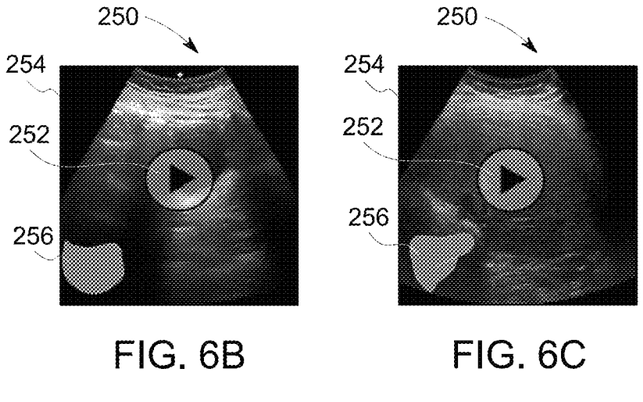
Figure 6D:
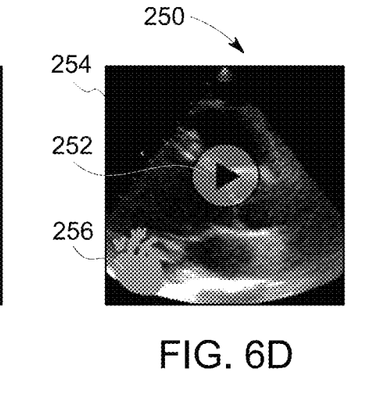
Figure 6E:
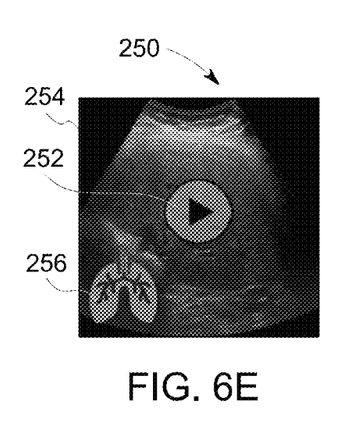
Figure 6F:
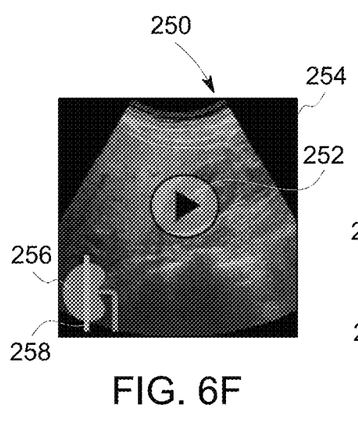
Figure 6G:
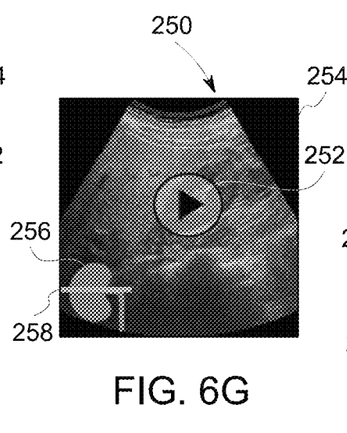

In addition to the representation of the organ/anatomical structure via the organ icon 256, when the processor 222,232 is operated in block 306 to detect the view/view orientation/view angle associated with organ/anatomical structure from which the image/video loop 214 is formed, in block 316 the processor 222,232 can provide an indication in the organ icon 256 of the detected view for the image/video loop 214. Referring to the exemplary embodiment of FIGS. 6F and 6G, when a particular view for the image/video loop 214 is detected by the processor 222,232, the organ icon 256 to be inserted into the thumbnail image 250 can include a view line 258. The view line 258 is positioned on the organ icon 256 in a representation of the view along which the organ/anatomical structure present in the image/video loop 214 is imaged/captured. Therefore, with the view line 258, in addition to the organ/anatomical structure information provided by the shape of the organ icon 256, the organ icon 256 also enables an individual to know what view of the indicated organ/anatomical structure is provided in the particular image/video loop 214 associated with the thumbnail image 250

Figure 6H:
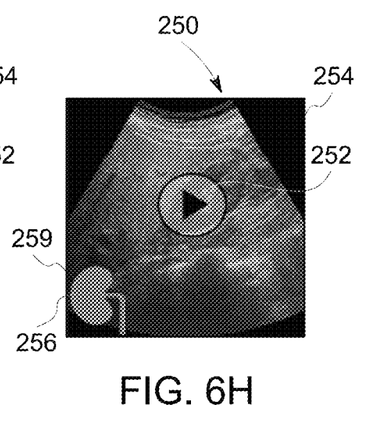

Referring now to FIGS. 3 and 6H, when the processor 222,232 additionally determines that an anomaly is present within the image/frames of the video loop 214 in block 308, in block 316 the processor 222,232 can provide an anomaly indication or modification 259 to the organ icon 256 of the presence of the anomaly within the image/video loop 214. In the illustrated exemplary embodiment, the anomaly indication is provided by modifying the organ icon 256 in some identifiable manner, such as by changing the color of the organ icon 256, by changing the size of the organ icon 256, by changing the brightness of the organ icon 256, by causing the organ icon 256 to flash or oscillate between different colors and/or brightness levels, or any other suitable manner to distinguish the organ icon 256 including an anomaly detection from an organ icon 256 without an anomaly detection.

In the case of either or both of the inclusion of the view line 258 and the anomaly modification in the organ icon 256, this information is stored along with the thumbnail image 250 as described previously, and can also be added to the custom data, i.e., meta-data and tags, stored in association with the image/video loop 214.

Figure 4:
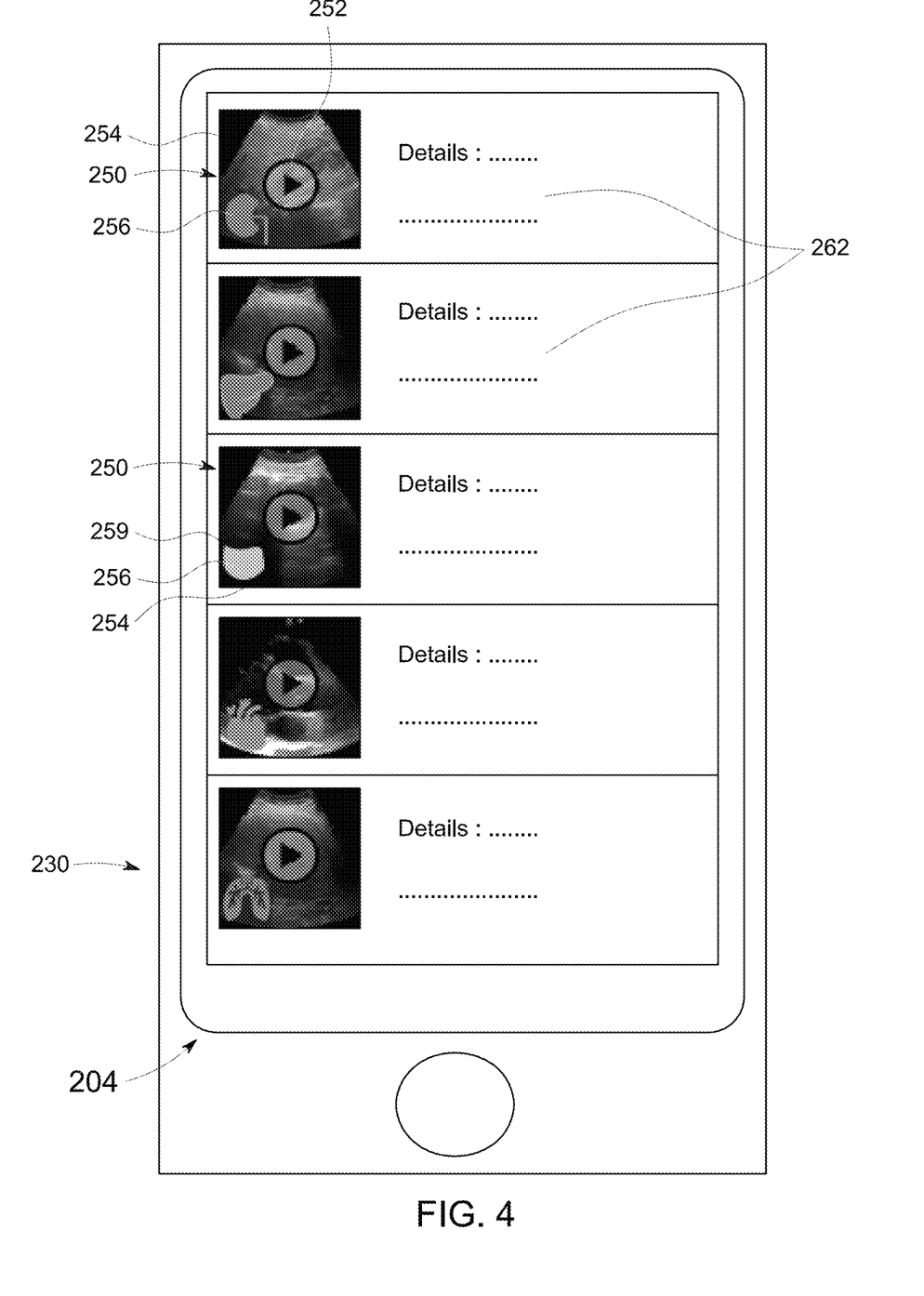
FIG. 4 is a schematic view of thumbnail images representing stored video loops presented on a display screen of a remote device in accordance with an embodiment.
Figure 5:
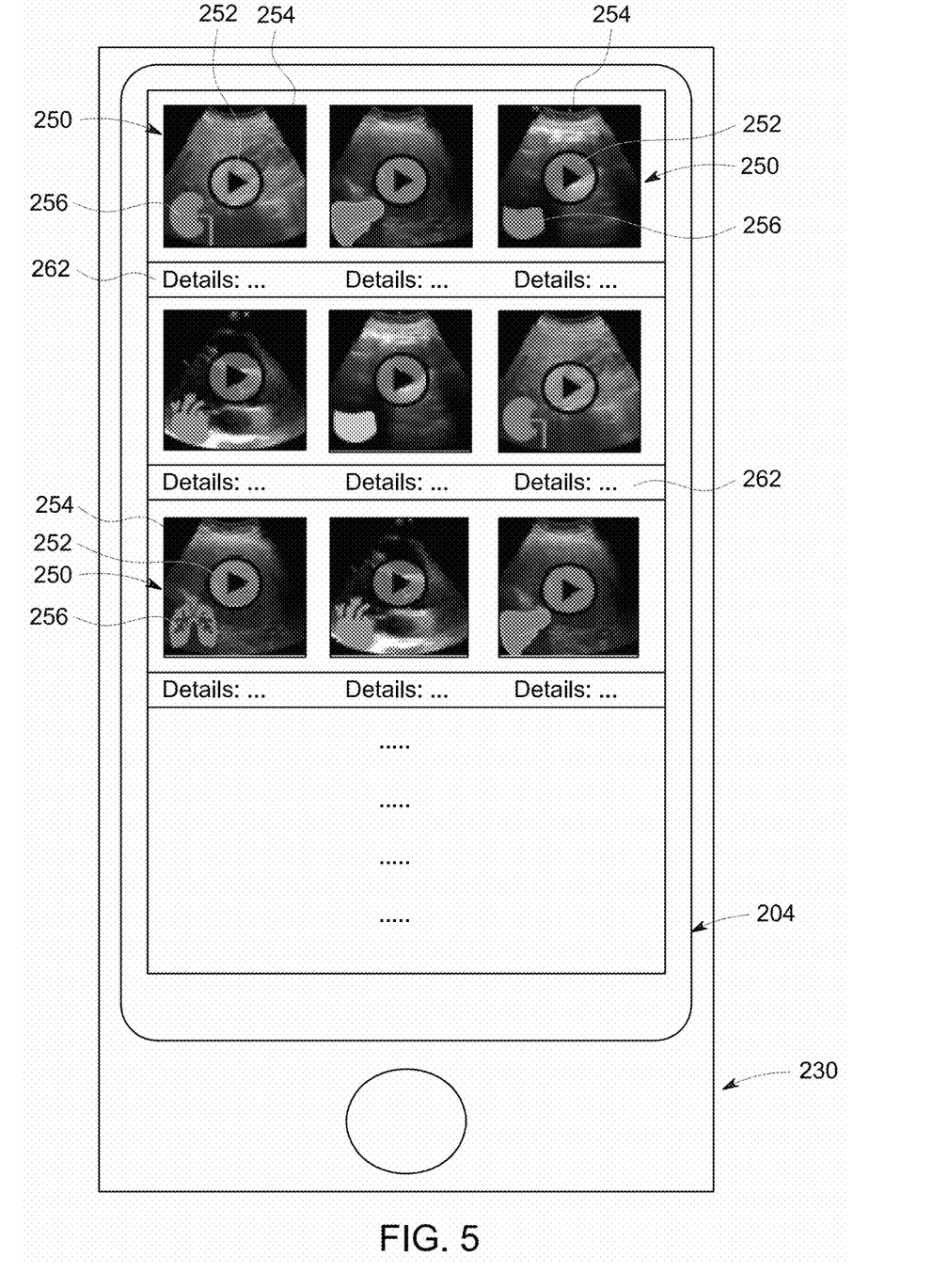
FIG. 5 is a schematic view of thumbnail images representing stored video loops presented on a display screen of a remote device in accordance with another embodiment.

Looking now at FIGS. 4 and 5, the display 204 of a remote device 230 is illustrated in which a number of thumbnail images 250 are presented with each thumbnail image 250 representing a particular image/video loop 214. The thumbnail images 250 are present in a list view (FIG. 4) or a grid view (FIG. 5) and illustrate how the organ icon 256 in each thumbnail image 250 provides a readily viewable display of the information concerning the organ(s)/anatomical structure(s) shown in each image/video loop 214, without the need to initiate the playback of each image/video loop 214. Further, the size of the displayed thumbnail images 250 also enables other information, text or details 262 regarding the individual image/video loop 214 to be presented along with the thumbnail image 250 to enhance the ability of the user to quickly review each displayed thumbnail image 250 in the list or grid to determine their relevancy to the search.

Figure 7:
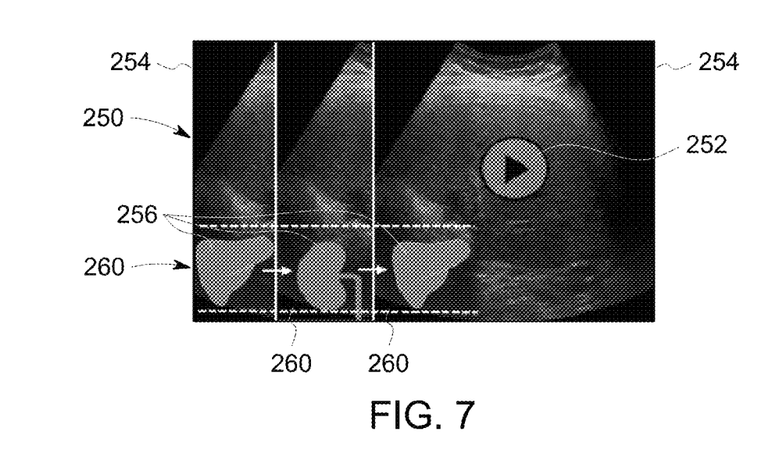
FIG. 7 is a schematic view of a thumbnail image identifying a stored video loop in accordance with an embodiment.

Looking now at FIGS. 3 and 7 when the processor 222,232 in block 304 detects a number of organs/anatomical structures that are present within the image/video loop 214, the processor 222,232 can create a multiple organ icon 260 to be presented within the thumbnail image 250 that provides an indication of each of the organs/anatomical structures identified in the image/video loop 214. In the illustrated exemplary embodiment, the multiple organ icon 260 is a cine or cycled loop of a display of the individual organ icons 256 representing the individual organs/anatomical structures detected within the image/video loop 214. In this manner, the multiple organ icon 260 provides an easy to interpret indication of the multiple organs/anatomical structures that are viewable within the image/video loop 214 identified by the thumbnail image 250 including the multiple organ icon 260.

Figure 8A:
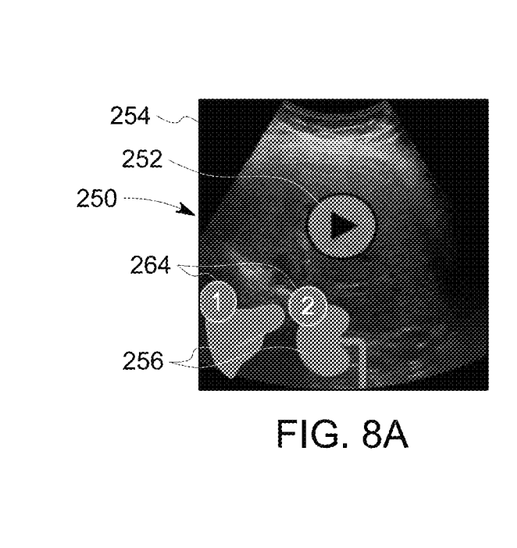
FIGS. 8A-8B are schematic views of thumbnail images identifying stored video loops in accordance with another embodiment.
Figure 8B:
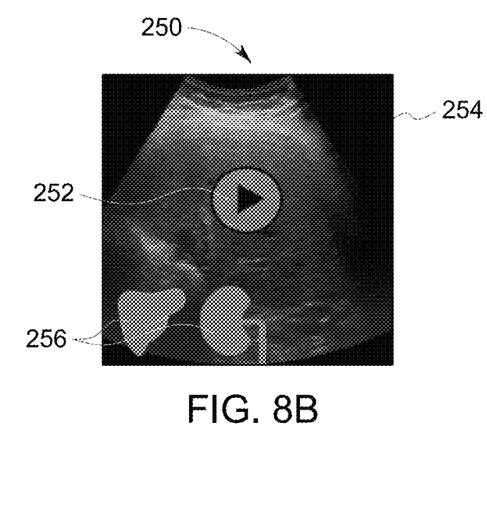

Referring now to FIGS. 3 and 8A-8B, in an alternative situation where multiple organs/anatomical structures are detected within a image/video loop 214, in block 304 the processor 222,232 can determine which organs/anatomical structures are present in over a threshold value of the frames of the video loop 214. Alternatively, for a single ultrasound image 214, the processor 222,232 can determine which organs/anatomical structures are present in the image 214 in over a threshold value for the area of the image 214. Once determined, the processor 222,232 can utilize a number of organ icons 256 within the single thumbnail image 250 that represent each of the organs/anatomical structures determined to be present in the image/video loop 214 that meet or exceed the threshold value. While any ordering of the organ icons 256 is contemplated as being within the scope of the present disclosure, in one exemplary embodiment the organ icons 256 can be ordered in the thumbnail image 250 with the leftmost organ icon 256 indicating the organ/anatomical structure most present in the frames of the image/video loop 214 and the rightmost organ icon 256 being present in the fewest frames of the image/video loop 214. The individual organ icons 256 can also each include a numerical indicator 264 that visually indicates the relative prominence of the particular organ/anatomical structure in the frames of the image/video loop 214 along with or as a replacement for the left to right ordering of the organ icons 256.

In addition to the multiple organ icons 256, in a thumbnail image 250 for an image/video loop 214 containing multiple organs/anatomical structures, the icons 256 can be individually displayed with representations of the view line 258 and/or anomaly indication 259 for each of the organ icons 256, if relevant to the particular organ icon 256. Alternatively, for the detection analyses performed in block 308 (anomaly detection), in an exemplary embodiment, if the processor 222,232 detects an anomaly in any of the individual frames of the video loop 214, the processor 222,232 can identify the entire video loop 214 as containing an anomaly.

Figure 9:
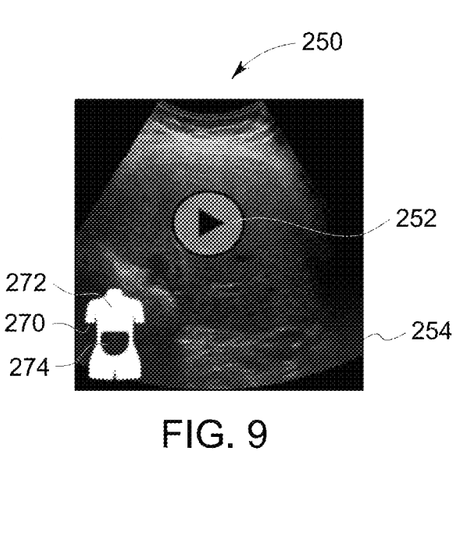
FIG. 9 is a schematic view of a thumbnail image identifying a stored video loop in accordance with an embodiment.

Looking now at FIG. 9, as an alternative for the indication of multiple organs/anatomical structures in the image/video loop 214 by using multiple organ icons 256, 260 in a thumbnail image 250, the thumbnail image 250 can include an anatomical region icon 270. The anatomical region icon 270 can be added to the thumbnail image 250 by the processor 222,232 in block 316 in situations where the processor 222,232 determines that the image/video loop 214 covers a number of organs/anatomical structures within a particular region of the anatomy, and the anatomical region icon 270 best indicates the information contained within the particular image/video loop 214. In the exemplary embodiment of FIG. 9, the anatomical region icon 270 is illustrated as a torso 272 with the abdomen 274 highlighted, indicating the image/video loop 214 is focused on the organs/anatomical structures within the abdomen 274 of the patient. In alternative exemplary embodiments, the anatomical region icon 270 can have other shapes representing other portions of the anatomy of the patient, such as a leg, arm, etc. Further, the anatomical region icon 270 can have multiple areas highlighted within the icon 270, or can have multiple icons 270 presented with the thumbnail image 250, similar to the multiple icons 256 in FIGS. 8A-8B.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for displaying information regarding the subject matter of an ultrasound image or ultrasound video loop on a display, the method comprising the steps of:
   providing the ultrasound image or the ultrasound video loop;
   detecting and identifying one or more organs in the ultrasound image or ultrasound video loop;
   creating a representative thumbnail image utilizing the ultrasound image or a frame of the ultrasound video loop;
   selecting an organ icon representing the one or more organs detected and identified in the ultrasound image or ultrasound video loop; and
   presenting the organ icon in association with the thumbnail image on the display,
   wherein the step of detecting and identifying the one or more organs in the ultrasound image or ultrasound video loop comprises analyzing the ultrasound image or individual frames of the ultrasound video loop to locate one or more organs in the ultrasound image or individual frames of the ultrasound video loop, and wherein the step of analyzing the ultrasound image or individual frames of the ultrasound video loop comprises employing at least one of an algorithm, an artificial intelligence or a machine learning method applying one or more of image segmentation, image classification or object localization to the ultrasound image or the ultrasound video loop to locate one or more organs within the ultrasound image or individual frames of the ultrasound video loop.

2. The method of claim 1, wherein the step of analyzing the ultrasound image or individual frames of the ultrasound video loop comprises:
   determining an area of the ultrasound image in which the one or more organs are located; and
   assessing whether the area exceeds a predetermined threshold value for the presence of the one or more organs in the ultrasound image.

3. The method of claim 1, wherein the step of analyzing the ultrasound image or individual frames of the ultrasound video loop comprises:
   determining a number of individual frames of the ultrasound video loop in which the one or more organs are located; and
   assessing whether the number of individual frames exceeds a predetermined threshold value for indicating the presence of the one or more organs in the ultrasound video loop.

4. The method of claim 1, wherein the step of presenting the organ icon in association with the thumbnail image comprises placing the organ icon within the thumbnail image.

5. The method of claim 1, wherein the step of selecting an organ icon comprises selecting a multiple organ icon corresponding to each of the one or more organs detected and identified in the ultrasound image or ultrasound video loop.

6. The method of claim 1, further comprising the steps of:
   detecting a view of the one or more organs present in the ultrasound image or ultrasound video loop; and
   providing an indication of the view on the organ icon in association with the thumbnail image.

7. The method of claim 6, wherein the step of detecting the view associated with the one or more organs in the ultrasound image or ultrasound video loop comprises implementing at least one of an algorithm, an artificial intelligence or a machine learning method applying image classification to the ultrasound image or the ultrasound video loop to detect the view in the ultrasound image or the ultrasound image video loop.

8. The method of claim 1, further comprising the steps of:
   providing results of the analysis of the ultrasound image or the ultrasound video loop to identify one or more organs within the ultrasound image or individual frames of the ultrasound video loop;
   detecting an anomaly in the ultrasound image or ultrasound video loop; and
   providing an indication of the anomaly on the organ icon in association with the thumbnail image.

9. The method of claim 8, wherein the step of detecting the anomaly in the ultrasound image or ultrasound video loop comprises implementing at least one of an algorithm, an artificial intelligence or a machine learning method employing at least one of an algorithm, an artificial intelligence or a machine learning method applying one or more of image segmentation, image classification or object localization to the ultrasound image or the ultrasound video loop to detect the anomaly in the ultrasound image or the ultrasound image video loop.

10. The method of claim 1, further comprising the step of storing the thumbnail image with the organ icon in an electronic memory in association with the ultrasound image or ultrasound video loop.

11. The method of claim 10, further comprising the steps of:
   creating electronic file search-identifiable information relating to the one or more organs detected in the ultrasound image or ultrasound video loop; and
   storing the electronic file search-identifiable information in the electronic memory in association with the ultrasound image or ultrasound video loop and the thumbnail image with the organ icon.

12. An imaging system for displaying images obtained by the imaging system on a display, the imaging system comprising:
   an imaging probe adapted to obtain image data on an object to be imaged;
   a processor operably connected to the probe to form one of an image or an image video loop from the image data and to form a thumbnail image representative of the image or image video loop; and
   a display operably connected to the processor for presenting the image or the image video loop on the display,
   wherein the processor is configured:
      to implement at least one of an algorithm, an artificial intelligence or a machine learning method applying one or more of image segmentation, image classification or object localization to the image or the image video loop to detect and identify one or more organs in the image or the image video loop,
      to select an organ icon from a stored list of organ icons representing the one or more organs detected and identified in the ultrasound image or ultrasound video loop, and
      to present the organ icon in association with the thumbnail image of the image or image video loop on the display, and
   wherein the detecting and identifying of the one or more organs within the image or image video loop comprises determining if the one or more organs are present in at least over a threshold value of a total area forming the image or of total frames forming the video loop.

13. The imaging system of claim 12, wherein the processor is configured to determine if a percentage of a total area of the image in which the one or more organs are detected and identified, or a percentage of a total number of frames in the image video loop in which the one or more organs are detected and identified exceeds a predetermined threshold.

14. The imaging system of claim 12, wherein the processor is configured to select a multiple organ icon if more than one organ is detected and identified in the image or image video loop.

15. The imaging system of claim 12, wherein the processor is configured to implement at least one of an algorithm, an artificial intelligence or a machine learning method applying one or more of image segmentation, image classification or object localization to the image or the image video loop to detect a view associated with the one or more organs in the image or the image video loop, and to modify the organ icon with an indication of the view.

16. The imaging system of claim 12, wherein the processor is configured to implement at least one of an algorithm, an artificial intelligence or a machine learning method applying one or more of image segmentation, image classification or object localization to the image or the image video loop to detect one or more anomalies in the image or the image video loop, and to modify the organ icon with an indication of the one or more anomalies.

17. The imaging system of claim 12, wherein the imaging system comprises an electronic memory, and wherein the processor is configured to create search-identifiable information relating to the one or more organs detected and identified in the ultrasound image or ultrasound video loop, and to store the search-identifiable information in the electronic memory in association with the image or the image video loop and the thumbnail image with the organ icon.

18. An imaging system for displaying images obtained by the imaging system on a display, the imaging system comprising:
- an imaging probe adapted to obtain image data on an object to be imaged;
- a processor operably connected to the probe to form one of an image or an image video loop from the image data and to form a thumbnail image representative of the image or image video loop;
- an electronic memory operably connected to the processor; and
- a display operably connected to the processor for presenting the image or the image video loop on the display, wherein the processor is configured:
- to implement at least one of an algorithm, an artificial intelligence or a machine learning method applying one or more of image segmentation, image classification or object localization to the image or the image video loop to detect and identify one or more organs in the image or the image video loop,
- to select an organ icon from a stored list of organ icons representing the one or more organs detected and identified in the ultrasound image or ultrasound video loop, to store the thumbnail and organ icon in association with the image or image video loop in the electronic memory, and
- to present the organ icon in association with the thumbnail image of the image or image video loop on the display, and wherein the detection and identification of the one or more organs within the image or image video loop comprises determining if the one or more organs are present in at least 25% of a total area of an image or in at least 15% of the frames of a video loop.

19. The imaging system of claim 18, wherein the processor is configured to create search-identifiable information relating to the one or more organs detected and identified in the ultrasound image or ultrasound video loop, and to store the search-identifiable information in the electronic memory in association with the image or the image video loop and the thumbnail image with the organ icon.

* * * * *